United States Patent [19]

Moalem

[11] Patent Number: 5,752,507

[45] Date of Patent: May 19, 1998

[54] METHOD AND APPARATUS FOR DIFFERENTIAL LUNG VENTILATION

[76] Inventor: Jacob Moalem, 14 Montefiori St., Petach Tikva 49364, Israel

[21] Appl. No.: 832,837

[22] Filed: Apr. 4, 1997

[51] Int. Cl.$^6$ ................................................ A61M 16/00
[52] U.S. Cl. ................................. 128/204.21; 128/204.18
[58] Field of Search ........................ 128/204.18, 204.21, 128/204.26, 204.28, 205.24, 203.12, 203.25, 207.15, 207.16; 604/94, 104, 131

[56] References Cited

U.S. PATENT DOCUMENTS 4,233,984 11/1980 Walling .
4,598,706 7/1986 Darowski et al. .

OTHER PUBLICATIONS

Advertisement for TYLAN Mass Flow Controllers, no date.
Pace et al, "Differential Lung Ventilation After Unilateral Hydrochloric Acid Aspiration in the Dog", *Critical Care Med.*, vol. 11, No. 1, pp. 17–20 (1983).
East, et al., "Synchronous Versus Asynchronous Differential Lung Ventilation with PEEP after Unilateral Acid Aspiration in the Dog", *Critical Care Med.*, vol. 11, No. 6, pp. 441–444 (1983).
Nishimura, et al., "High–Frequency Jet Ventilation for Differential Lung Ventilation", *Critical Care Med.*, vol. 12, No. 9, pp. 840–841 (1984).

Advertisement for PORTEX Endobronchial Twin Lumen Tube, no date.

*Primary Examiner*—Vincent Millin
*Assistant Examiner*—Robert N. Wieland
*Attorney, Agent, or Firm*—Mark M. Friedman

[57] ABSTRACT

Method and apparatus for ventilating lungs of different compliance with a predetermined ratio of volumes using one respirator are provided. The method comprises: (a) pumping fluid into a first and second inspiratory passageways, the first passageway being in fluid communication with a more resistive lung and the second passageway being in fluid communication with a less resistive lung; (b) regulating the flow of fluid within the second passageway by means of a regulating element, the regulating element being automatically controlled by means of a controlling element according to the volumes expired by the first and second lungs. The apparatus includes: (a) a single respirator; (b) a first and second inspiratory passageways in fluid communication with respective first and second lungs, the first lung being more resistive to ventilation than the second lung; (c) a pneumatic regulating element connected to the second passageway for regulating the flow of fluid within the second passageway; and (d) a controlling element for automatically controlling the regulating element based on the volumes expired by the first and second lungs.

33 Claims, 2 Drawing Sheets

METHOD AND APPARATUS FOR DIFFERENTIAL LUNG VENTILATION

FIELD AND BACKGROUND OF THE INVENTION

The present invention relates to method and apparatus for differential ventilation of user's lungs and, more particularly, to method and apparatus for selectively ventilating two lungs of different compliance with a predetermined ratio of gas volumes. Further, the present invention provides method and apparatus for selectively treating lungs suffering from gas leakage by selectively ventilating the two lungs with a predetermined ratio of gas flows.

Diseases characterized in changes of a lung's compliance include: (a) diseases wherein fluids accumulate within and adjacent the alveoli, which fluids causes the lung to be less compliant and more resistant to ventilation. Examples are: bronchopleural fistulae, pneumonia, pulmonary edema and hemorrhage; (b) abnormal development or destruction of the alveolar tissue participating in the process of gas exchange; (c) destruction of elastic tissue and formation of connective tissue within the lungs.

Leakage of gases from a lung may result from tearing or perforation of the lung. Such leakage may prevent ventilation of specific areas within the lung.

The above diseases may be classified into two main groups: diseases wherein a lung's resistance to ventilation increases with relation to a healthy lung; and diseases wherein a lung's resistance to ventilation decreases with relation to a healthy lung.

Thus, a unilateral lung disease may cause the injured lung to become more resistive to ventilation, or alternatively, less resistive to ventilation with relation to a healthy lung. Consequences of such a unilateral disease include increase in $CO_2$ concentration and decrease in blood oxidation within the injured lung.

Ventilation of two lungs having different compliance at a certain higher pressure, using one breathing machine, so as to treat the problem of oxidation within the injured lung may cause further damage due to excessive pressure on the healthy lung.

Various attempts have been made to provide methods and devices for selectively ventilating two lungs of different resistance to ventilation. However, most of these methods and devices use two breathing machines, each for ventilating a specific lung at a different gas pressure, the breathing machines being synchronized by means of a microprocessor. However, such configuration is cumbersome, expensive, and may suffers from low reliability.

Other attempts have been made to provide methods and devices for differential lung ventilation which use a single breathing machine. An example is disclosed in U.S. Pat. No. 4,598,706. However, none of these disclosures provides method and apparatus which enable to selectively ventilate two lungs of different compliance such that the ratio of tidal volumes ventilated by the lungs is predetermined and continuously controlled. Further, none of these disclosures provides method and apparatus wherein differential ventilation of the lungs at a given cycle is regulated according to the ratio of tidal volumes ventilated by the lungs at a preceding cycle.

There is thus a widely recognized need for, and it would be highly advantageous to have, method and apparatus for differential ventilation of lungs having different compliance, which allows to selectively ventilate the lungs according to a predetermined ratio of tidal volumes by using a single respirator. There is further a recognized need for such method and apparatus wherein differential ventilation of the lungs at a given cycle is regulated according to the ratio of tidal volumes ventilated by the lungs at a preceding cycle.

SUMMARY OF THE INVENTION

According to the present invention there is provided method and apparatus for selectively ventilate lungs of different compliance with a predetermined ratio of gas volumes by using a single respirator.

Method and device according to the present invention enable, for example, to ventilate each lung at a specific pressure, thereby forcing an injured lung to ventilate a certain minimal tidal volume while maintaining a normal tidal volume at the normal lung, by using a single respirator.

A method according to the present invention comprises the steps of:

(a) pumping fluid into a first and second inspiratory passageways by using a single respirator, the first inspiratory passageway being in fluid communication with a first lung and the second inspiratory passageway being in fluid communication with a second lung, the first lung being more resistive to ventilation than the second lung;

(b) regulating the flow of fluid within the second passageway by means of a regulating element so as to ventilate the first and second lungs at a predetermined ratio of volumes.

The regulating element may be a pneumatic resisting element. Alternatively, the regulating element may be a pressure regulator. Alternatively, the regulating element may be a flow regulator.

According to further features in preferred embodiments of the invention described below, the method further comprises the step of: measuring a first volume of fluid expired by the first lung and a second volume of fluid expired by the second lung; and comparing the first and second volumes.

Further, the regulation may be proportional to the difference between the first volume and the second volume. Alternatively, the regulation may be proportional to the ratio between the first volume and the second volume.

According to still further features in the described preferred embodiments, the measurement is performed at a given respiratory cycle and the regulation is performed at a subsequent respiratory cycle.

According to one preferred embodiment, the measurement is performed at a given expiratory phase and the regulation is performed at a subsequent inspiratory phase. Alternatively, the measurement is performed at a given expiratory phase and the regulation is performed during said expiratory phase.

Preferably, the regulation is automatically performed by means of a controlling element electrically connected to the regulating element.

According to another embodiment the method comprises: measuring a first volume of fluid pumped within the first inspiratory passageway and a second volume of fluid pumped within the second inspiratory passageway; and comparing the first and second volumes.

According to yet another embodiment the method comprises: measuring a first flow-rate of fluid flowing within the first inspiratory passageway and a second flow-rate of fluid flowing within the second inspiratory passageway; and comparing the first and second flow-rates.

An apparatus according to the present invention preferably comprises:

(a) a single respirator;
(b) a first and second inspiratory passageways connected to the respirator, the first inspiratory passageway being in fluid communication with a first lung and the second inspiratory passageway being in fluid communication with a second lung;
(c) a regulating element connected to the second inspiratory passageway for regulating the flow of fluid within the second passageway;
(d) a first expiratory passageway in fluid communication with the first lung and a second expiratory passageway in fluid communication with the second lung;
(e) a first volume measuring element connected to the first expiratory passageway for measuring a first volume of fluid expired by the first lung and a second volume measuring element connected to the second expiratory passageway for measuring a second volume of fluid expired by the second lung;
(f) a controlling element electrically connected to the first and second volume measuring elements and to the regulating element for automatically controlling the regulating element based on the first and second volumes measured by the first and second volume measuring elements, such that a predetermined ratio is achieved between the first volume of fluid expired by the first lung and the second volume of fluid expired by the second lung.

The present invention successfully addresses the shortcomings of the presently known configurations by providing method and apparatus which enable to selectively ventilate lungs of different compliance at a predetermined ratio of volumes by using a single respirator. Further, the present invention enables to continuously and automatically regulate the ratio of ventilated volumes at a given respiratory cycle based on the volumes ventilated by the lungs at the preceding respiratory cycle.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a method and apparatus for selectively ventilating user's lungs having different compliances with a predetermined ratio of gas volumes. Further, the present invention is of method and apparatus wherein differential ventilation of the lungs at a given cycle is regulated according to the ratio of volumes ventilated by the lungs at a preceding cycle.

The principles and operation of method and apparatus according to the present invention may be better understood with reference to the drawings and the accompanying description.

Figure 1:
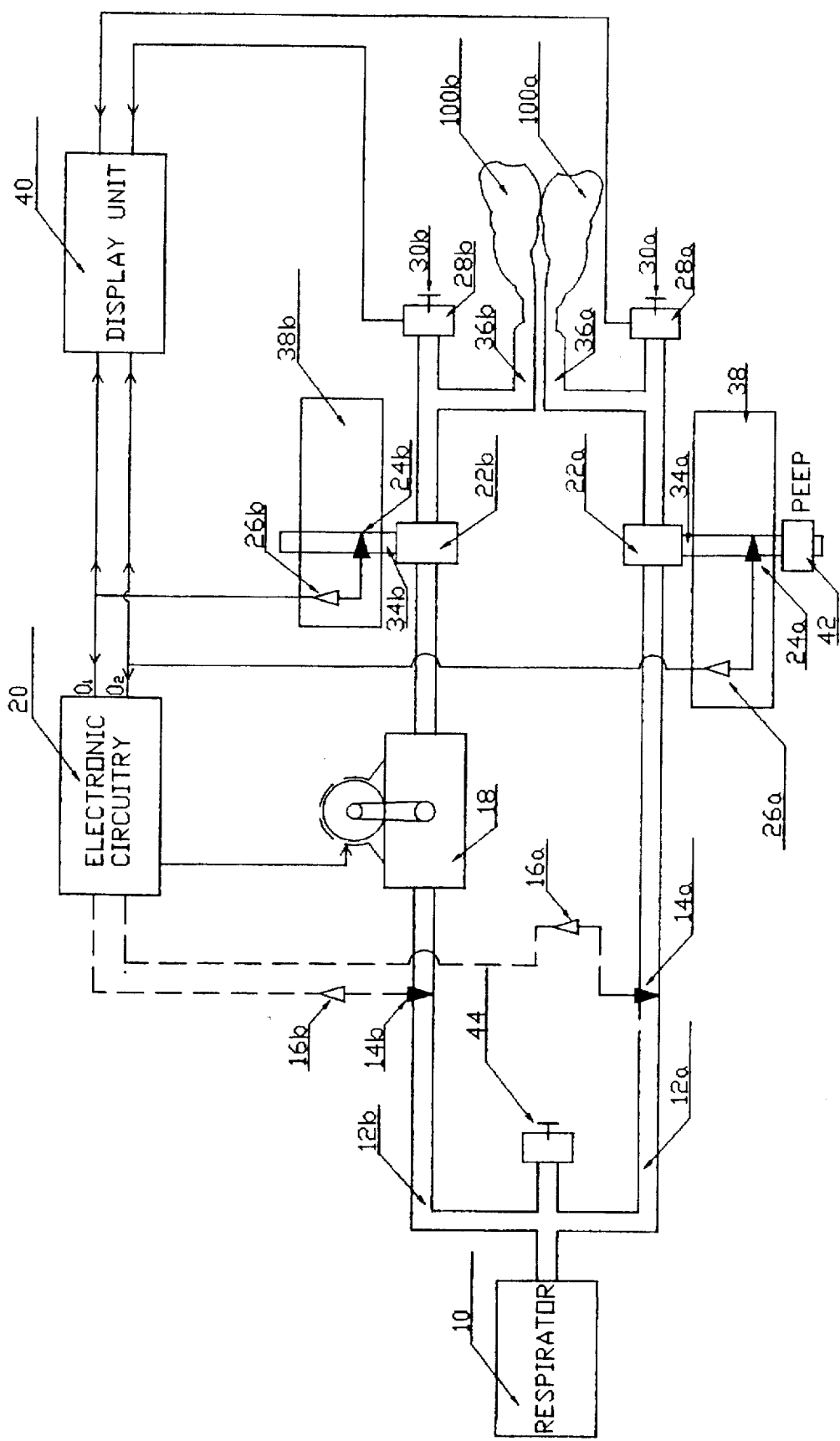
FIG. 1 is a schematic illustration of a device according to the present invention.

Referring now to the drawings, FIG. 1 illustrates an apparatus according to the present invention. As shown in the figure, the apparatus includes a single respirator 10 for supplying fluid, such as air, at a certain pressure to lungs 100a and 100b of a patient.

Respirator 10 is connected via inspiratory passageways 12a and 12b to respective endobronchial tubes 36a and 36b, the endobronchial tubes being in fluid communication with lungs 100a and 10b, respectively. Endobronchial tubes 36a and 36b may be any of the endobronchial tubes known in the art.

The specific example shown in the figure refers to lung 100a as the more resistive lung, and lung 100b as the less resistive lung.

The higher resistance to ventilation of lung 100a may result from any injury which decrease the compliance of the lung, such as fluid accumulation within the lung, formation of connective tissue in place of the elastic tissue, and the like. Lung 100b may be a normal lung or a less injured, and therefore more compliant lung.

Alternatively, the lower resistance to ventilation of lung 100b may result, for example, from tearing or perforation of the lung. In this case, lung 100a is a normal lung or a less injured lung.

As shown in FIG. 1, a pneumatic regulating element 18 is connected in serial connection to lung 100b, which is the less resistive lung. Pneumatic regulating element 18 may be a resisting element such as a conventional valve enabling a continuous or discrete flow of fluid.

The electrical equivalent resistance of regulating element 18 is preferably equal to the difference between the equivalent resistances of lung 100a and lung 100b. Thus, the total equivalent resistance of passageway 12a and lung 100a equals the total equivalent resistance of passageway 12b and lung 100b. This way, a single respirator outputting a certain pressure may be used to ventilate the lungs at equal volumes, whereas lung 100a is being ventilated at a higher pressure and lung 100b is being ventilated at a lower pressure.

The ratio of the volumes ventilated within lungs 110a and 100b depends on the selected resistance of regulating element 18. Thus, an apparatus according to the present invention enables to achieve a predetermined ratio of ventilated volumes within lungs 100a and 100b, simply by changing the resistance of regulating element 18.

According to another configuration, regulating element 18 may be a conventional pressure regulator. Alternatively, regulating element 18 may be a conventional flow controller.

As shown in the figure, an apparatus according to the present invention further includes controlling electronic circuitry 20 electrically connected to regulating element 18 for continuously controlling regulating element 18. The control of regulating element 18 is preferably carried out according to the rate of tidal volumes expired by lung 100a and 10b.

Accordingly, an apparatus according to the present invention preferably includes volume-measuring elements, 38a and 38b, connected to respective expiratory passageway, 34a and 34b, for measuring volumes expired by lungs 100a and 100b, respectively.

Volume-measuring elements 38a and 38b may be conventional volume-meters.

Alternatively, volume-measuring elements 38a and 38b may include respective flow-meters, 24a and 24b, and respective integrators, 26a and 26b, for integrating the flow deflated by each lung over a time interval and thereby providing volume measurements. However, when using flow meters and integrators, the time interval within which the flow measurements are carried out is of a great significance. Since the more resistive lung is ventilated at a higher pressure, the gases are expired from such lung at a higher flow rate, particularly at the beginning of the expiratory phase. Therefore, a flow measurement taken at a time interval during the beginning of the expiratory phase may show a false rate of expired volumes.

When treating lungs suffering from tearing or perforation, volume or flow measurements are preferably taken at the inspiratory, rather than the expiratory path. Accordingly, as shown in FIG. 1, flow meters 12a and 12b and respective integrators 16a and 16b are preferably connected to inspiratory passageways 12a and 12b, for measuring flows or volumes of gases pumped into the lungs.

Thus, an apparatus according to the present invention preferably includes volume measuring elements both at the inspiratory and expiratory passageways so as to enable treatment of various diseases. Such configuration enables, for example, to identify cases wherein gases are leaked from or accumulated within the lungs as well as to quantitate such leakage or accumulation.

When treating diseases wherein the more injured lung is more resistive to ventilation, electronic circuitry 20 preferably controls the operation of regulating element 18 according to the rate of tidal volumes expired by lungs 100a and 100b, which is given by the rate of volumes measured by volume measuring elements 38a and 38b.

When treating diseases wherein the more injured lung is less resistive to ventilation, electronic circuitry 20 preferably controls the operation of regulating element 18 according to the rate of flows or volumes pumped into lungs 100a and 100b, which is given by the rate of flows or volumes measured by flow-meters 14a and 14b and integrators 16a and 16b.

Electronic circuitry 20 may compare the values of the volumes measured by volume measuring elements 38a and 38b and determine the difference between such values.

In the event that such a difference exists, electronic circuitry 20 sends a signal to regulating element 18 so as to compensate for the difference. When regulating element 18 is a pneumatic resisting element, the signal sent by electronic circuitry 20 changes the resistance of the resisting element. When regulating element 18 is a pressure regulator, the signal sent by electronic circuitry 20 changes the pressure produced by the pressure regulator.

The compensation may be continuously carried out during the same expiratory phase. However, in order to prevent the system from reaching instability due to changes over time of the ratio of the volume measured, the compensation is preferably performed at the inspiratory phase of the next expiratory cycle. This way, the compensation is carried out only after the entire tidal volumes expired by each lung are measured.

Alternatively, electronic circuitry 20 may compare the values of the volumes or flow-rates measured by flow-meters 14a and 14b and respective integrators 16a and 16b, and determine the difference between such values. In the event that such a difference exists, electronic circuitry 20 sends a signal to regulating element 18 so as to compensate for the difference. The compensation may be carried out during the same inspiratory phase. Alternatively, the compensation may be carried out during the next expiratory phase of the same respiratory cycle.

Preferably, 3/2 pneumatic valves 22a and 22b are used to separate passageways 12a and 12b from the respective expiratory passageways 34a and 34b. Valves 22a and 22b feature two states: a first state wherein fluid communication is established between inspiratory passageways, 12a and 12b, and the respective endobronchial tubes, 36a and 36b; and a second state wherein fluid communication is established between endobronchial tubes, 36a and 36b, and the respective expiratory passageways, 34a and 34b. Pneumatic valves 22a and 22b may be any of the 3/2 pneumatic valves known in the art, such as electrically controlled or pressure regulated pneumatic valves.

According to another configuration (not shown) unidirectional valves may be used to selectively direct the fluid within inspiratory passageways 12a and 12b, and within expiratory passageways 34a and 34b.

As shown in the figure, valves 22a and 22b are preferably placed as close as possible to the respective lungs 100a and 10b, so as to minimize the "dead space", i.e. the volume wherein inspired gases are mixed with expired gases, thereby providing more accurate measurements of volumes and flows of expired gases.

An apparatus according to the present invention preferably includes pressure meters, 28a and 28b, for measuring pressures within the respective lungs, 100a and 100b. Further, the apparatus preferably includes maximal threshold pressure valves, 30a and 30b, so as to prevent the formation of excessive pressure within lungs 100a and 10b. An additional maximal threshold pressure valve 44 is preferably connected to respirator 44.

Further, a positive-end-expiratory pressure (PEEP) valve may be placed at the end of expiratory passageway 34a, so as to maintain a minimal desired pressure within lung 100. An additional PEEP valve (not shown) may be placed at the end of expiratory passageway 34b.

An apparatus according to the present invention preferably includes a display unit 40 electrically connected to volume-measuring elements 38a and 38b and to electronic circuitry 20, for continuously displaying clinical parameters such as: expired volumes measured by volume measuring elements 38a and 38b; pressures within lungs 100a and 100b as measured by pressure-meters 28a and 28b, and the like.

Figure 2:
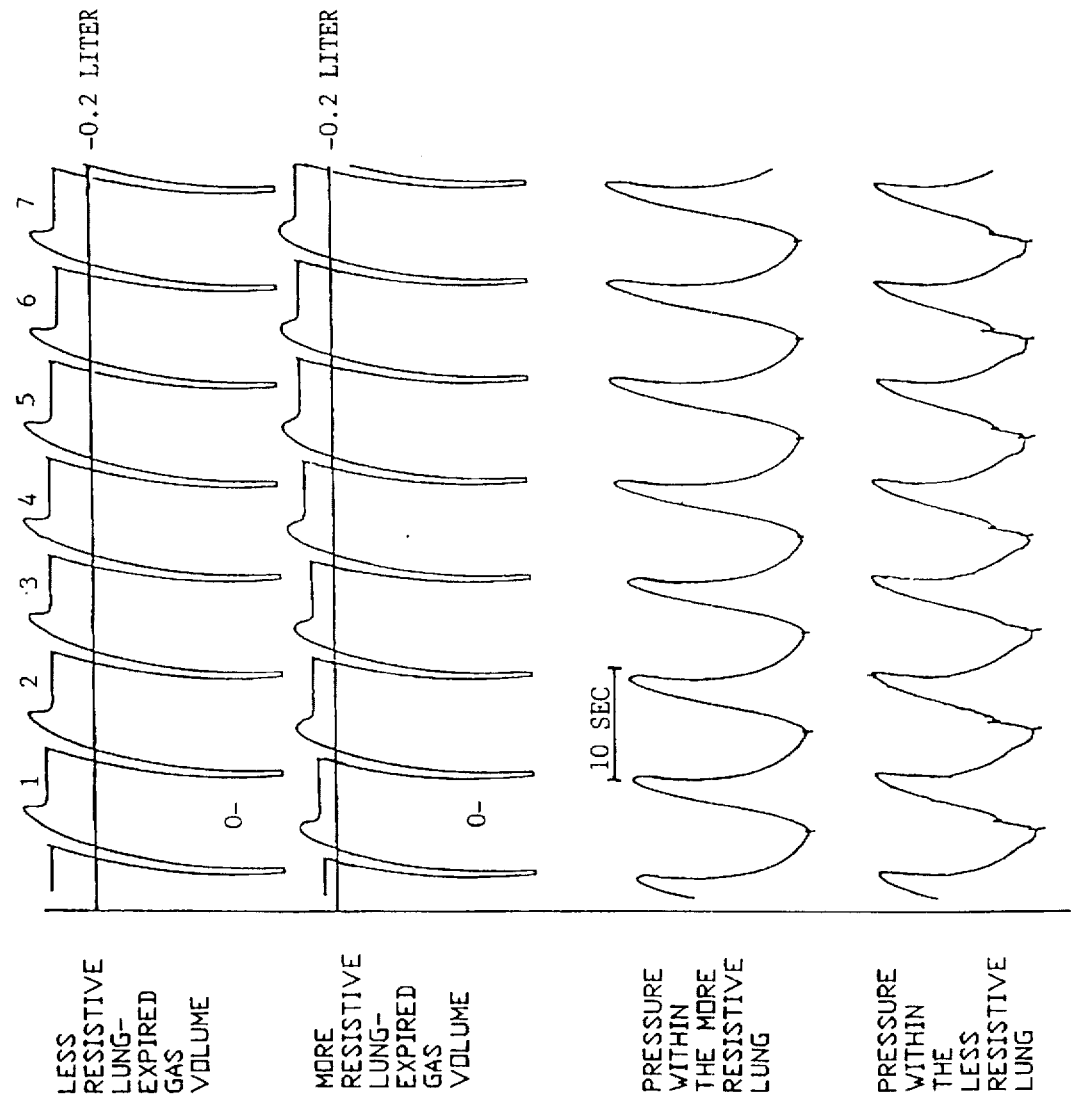
FIG. 2 is an example of experimental results illustrating the operation of method and device according to the present invention.

FIG. 2 shows experimental results illustrating the operation of method and apparatus according to the present invention. The results shown refer to a disease wherein the more resistive lung is an injured lung, and the less resistive lung is a normal lung. As shown in the figure, the gas volume ventilated by the injured lung (lung 100a) during the first respiratory cycle (denoted as 1) is much smaller than the gas volume ventilated by the normal lung (lung 10b). During the next respiratory cycles (denoted as 2-7) the injured lung is ventilated at higher pressures so as to achieve a minimal threshold of ventilation within the lung. Simultaneously, the difference between the measured expired volumes is compensated for, such that the gas volumes ventilated by the injured lung (lung 100a) increase, whereas the gas volumes ventilated by the normal lung (lung 100b) are preferably maintained at a constant value, or are slightly decrease. At the last respiratory cycle (denoted as 7) the gas volume ventilated by the injured lung approximately equals the gas volume ventilated by the normal lung, both ventilated volumes featuring a desired value. As shown in the figure, the pressure within the normal lung is approximately maintained at a constant value due to compensation.

Thus, method and apparatus according to the present invention enable, for example, to increase ventilation within the injured lung while maintaining a normal value of ventilation within the normal lung, using a single respirator.

Method and apparatus according to the present invention operate as follows:

(a) respirator 10 pumps air into inspiratory passageways 12a and 12b. Pneumatic valves 22a and 22b are set to allow selective fluid communication between inspiratory passageways, 12a and 12b, and the respective endobronchial tubes, 36a and 36b;

(b) At the next expiratory phase, valves 22a and 22b are set to allow selective fluid communication between endobronchial tubes, 36a and 36b, and the respective expiratory passageways, 34a and 34b. During said expiratory phase volume-measuring elements 38a and 38b measure the volumes expired by lungs 100a and 10b, respectively. Preferably, the flows of the expired gases are measured by flowmeters 24a and 24b, and are then integrated over a time interval which equals the entire time of the expiratory phase by means of integrators 26a and 26b;

(c) The results of the measurements are then transferred to controlling electronic circuitry 20. Electronic circuitry 20 preferably compares the results. In the event that a difference between the volumes measured exists, electronic circuitry 20 sends a signal to pneumatic regulating element 18 so as to compensate for the difference. Preferably, the compensating signal is sent to regulating element 18 at the next inspiratory phase.

After several cycles of compensation the system reaches a steady state wherein the tidal volumes ventilated by lungs 100a and 100b are preferably equal, thereby enabling symmetrical ventilation of the lungs.

While the invention has been described with respect to a limited number of embodiments, it will be appreciated that many variations, modifications and other applications of the invention may be made.

What is claimed is:

1. A method for ventilating user's lungs at a predetermined ratio of volumes, comprising the steps of:
    (a) pumping fluid into a first and second inspiratory passageways by using a single respirator, said first inspiratory passageway being in fluid communication with a first lung and said second inspiratory passageway being in fluid communication with a second lung, the first lung being more resistive to ventilation than the second lung;
    (b) regulating the flow of fluid within said second passageway by means of a regulating element so as to ventilate said first and second lungs at a predetermined ratio of volumes.

2. The method of claim 1, further comprising: measuring a first volume of fluid expired by said first lung and a second volume of fluid expired by said second lung; and comparing said first and second volumes.

3. The method of claim 2, wherein said regulation is proportional to the difference between said first volume and said second volume.

4. The method of claim 2, wherein said regulation is proportional to the ratio between said first volume and said second volume.

5. The method of claim 2, wherein said measurement is performed at a given respiratory cycle and said regulation is performed at a subsequent respiratory cycle.

6. The method of claim 2, wherein said measurement is performed at a given expiratory phase and said regulation is performed at a subsequent inspiratory phase.

7. The method of claim 2, wherein said measurement is performed at a given expiratory phase and said regulation is performed during said expiratory phase.

8. The method of claim 1, further comprising: measuring a first volume of fluid pumped within said first inspiratory passageway and a second volume of fluid pumped within said second inspiratory passageway; and comparing said first and second volumes.

9. The method of claim 8, wherein said regulation is proportional to the difference between said first volume and said second volume.

10. The method of claim 8, wherein said regulation is proportional to the ratio between said first volume and said second volume.

11. The method of claim 8, wherein said measurement is performed at a given inspiratory phase and said regulation is performed at a subsequent expiratory phase.

12. The method of claim 8, wherein said measurement is performed at a given inspiratory phase and said regulation is performed during said inspiratory phase.

13. The method of claim 1, further comprising: measuring a first flow-rate of fluid flowing within said first inspiratory passageway and a second flow-rate of fluid flowing within said second inspiratory passageway; and comparing said first and second flow-rates.

14. The method of claim 13, wherein said regulation is proportional to the difference between said first flow-rate and said second flow-rate.

15. The method of claim 13, wherein said regulation is proportional to the ratio between said first flow-rate and said second flow-rate.

16. The method of claim 13, wherein said measurement is performed at a given inspiratory phase and said regulation is performed at a subsequent expiratory phase.

17. The method of claim 13, wherein said measurement is performed at a given inspiratory phase and said regulation is performed during said inspiratory phase.

18. The method of claim 1, wherein said regulating element is a pneumatic resisting element connected to said second passageway.

19. The method of claim 1, wherein said regulating element is a pressure regulator connected to said second passageway.

20. The method of claim 1, wherein said regulating element is a flow regulator connected to said second passageway.

21. The method of claim 1, wherein said regulation is automatically performed by means of a controlling element electrically connected to said regulating element.

22. An apparatus for ventilating user's lungs at a predetermined ratio of volumes, comprising:
    (a) a single respirator;
    (b) a first and second inspiratory passageways connected to said respirator, said first inspiratory passageway being in fluid communication with a first lung and said second inspiratory passageway being in fluid communication with a second lung;
    (c) a regulating element connected to said second inspiratory passageway for regulating the flow of fluid within said second passageway;
    (d) a first expiratory passageway in fluid communication with the first lung and a second expiratory passageway in fluid communication with the second lung;
    (e) A first volume measuring element connected to said first expiratory passageway for measuring a first volume of fluid expired by the first lung and a second volume measuring element connected to said second expiratory passageway for measuring a second volume of fluid expired by the second lung;
    (f) a controlling element electrically connected to said first and second volume measuring elements and to said regulating element for automatically controlling said regulating element based on said first and second volumes measured by said first and second volume measuring elements.

such that a predetermined ratio is achieved between said first volume of fluid expired by the first lung and said second volume of fluid expired by the second lung.

23. The apparatus of claim 22, wherein at least one of said first and second volume measuring elements is a volume meter.

24. The apparatus of claim 22, wherein at least one of said first and second volume measuring elements includes a flow meter and an integrator.

25. The apparatus of claim 22, wherein said regulating element is a pneumatic resisting element.

26. The apparatus of claim 22, wherein said regulating element is a pressure regulator.

27. The apparatus of claim 22, wherein said regulating element is a flow regulator.

28. The apparatus of claim 22, further including at least one maximal threshold pressure valve.

29. The apparatus of claim 22, further including at least one pressure meter for measuring pressures within at least one of the first and second lungs.

30. The apparatus of claim 22, further including a first 3/2 pneumatic valve for separating said first inspiratory passageway from said first expiratory passageway and a second 3/2 pneumatic valve for separating said second inspiratory passageway from said second expiratory passageway.

31. The apparatus of claim 22, further including a first endobronchial tube in fluid communication with the first lung and a second endobronchial tube in fluid communication with the second lung.

32. An apparatus for ventilating user's lungs at a predetermined ratio of volumes, comprising:

(a) a single respirator;

(b) a first and second inspiratory passageways connected to said respirator, said first inspiratory passageway being in fluid communication with a first lung and said second inspiratory passageway being in fluid communication with a second lung;

(c) a regulating element connected to said second inspiratory passageway for regulating the flow of fluid within said second passageway;

(d) a first expiratory passageway in fluid communication with the first lung and a second expiratory passageway in fluid communication with the second lung;

(e) A first volume measuring element connected to said first inspiratory passageway for measuring a first volume of fluid flowing through said first inspiratory passageway and a second volume measuring element connected to said second inspiratory passageway for measuring a second volume of fluid flowing through said second inspiratory passageway;

(f) a controlling element electrically connected to said first and second volume measuring elements and to said regulating element for automatically controlling said regulating element based on said first and second volumes measured by said first and second volume measuring elements, such that a predetermined ratio is achieved between said first volume of fluid flowing through said first inspiratory passageway and said second volume of fluid flowing through said second inspiratory passageway.

33. An apparatus for ventilating user's lungs at a predetermined ratio of volumes, comprising:

(a) a single respirator;

(b) a first and second inspiratory passageways connected to said respirator, said first inspiratory passageway being in fluid communication with a first lung and said second inspiratory passageway being in fluid communication with a second lung;

(c) a regulating element connected to said second inspiratory passageway for regulating the flow of fluid within said second passageway;

(d) a first expiratory passageway in fluid communication with the first lung and a second expiratory passageway in fluid communication with the second lung;

(e) A first flow-meter connected to said first inspiratory passageway for measuring a first flow-rate of fluid flowing through said first inspiratory passageway and a second flow-meter connected to said second inspiratory passageway for measuring a flow-rate of fluid flowing through said second inspiratory passageway;

(f) a controlling element electrically connected to said first and second flow-meters and to said regulating element for automatically controlling said regulating element based on said first and second flow-rates measured by said first and second flow-meters, such that a predetermined ratio is achieved between said first flow-rate of fluid flowing through said first inspiratory passageway and said second flow-rate of fluid flowing through said second inspiratory passageway.

\* \* \* \* \*